United States Patent [19]

Houlihan

[11] 3,992,384
[45] Nov. 16, 1976

[54] SUBSTITUTED 1,2-DIHYDROBENZ[f]ISOQUINOLINE
[75] Inventor: William J. Houlihan, Mountain Lakes, N.J.
[73] Assignee: Sandoz, Inc., E. Hanover, N.J.
[22] Filed: Dec. 20, 1974
[21] Appl. No.: 534,685

Related U.S. Application Data

[63] Continuation-in-part of Ser. No. 407,104, Oct. 17, 1973, abandoned.

[52] U.S. Cl. .......................... 260/283 R; 260/283 S; 260/283 SY; 260/286 R; 260/288 CF; 260/289 C; 424/258
[51] Int. Cl.² ...................................... C07D 221/10
[58] Field of Search ...... 260/283 R, 289 C, 283 CF, 260/286 R

[56] References Cited
FOREIGN PATENTS OR APPLICATIONS
704,762  3/1941  Germany .......................... 260/283 R

OTHER PUBLICATIONS

Chem. Abstr., Decennial India, vol. 31–40, p. 4248, 1937–1946.

Kindler et al., Chem. Abst., vol. 33, 4596[8], (1939).

Kindler et al., Chem. Abst., vol. 36, 1956[1], (1941).

*Primary Examiner*—Nicholas S. Rizzo
*Assistant Examiner*—Mary C. Vaughn
*Attorney, Agent, or Firm*—Gerald D. Sharkin; Robert S. Honor; Thomas O. McGovern

[57] ABSTRACT

Substituted 1,2-dihydrobenz[f]isoquinolines, e.g., 4-(p-chlorophenyl)-1,2-dihydrobenz[f]isoquinoline, are prepared by cyclizing N-substituted-α-naphthylethylamines and are useful as non-estrogenic antifertility agents.

6 Claims, No Drawings

SUBSTITUTED 1,2-DIHYDROBENZ[F]ISOQUINOLINE

This application is a continuation-in-part of copending U.S. patent application, Ser. No. 407,104, filed Oct. 17, 1973 now abandoned.

This invention relates to 1,2-dihydro[f]isoquinoline derivatives. More particularly it relates to 4-aryl and 4-heterocyclic derivatives of benz[f]isoquinolines and their use in pharmaceutical compositions.

The compounds of this invention may be represented by the following formula:

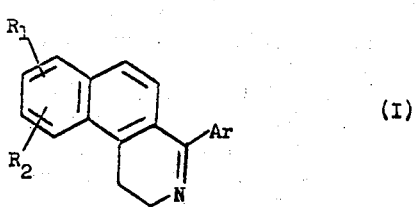

where
$R_1$ and $R_2$ each independently represent hydrogen or lower alkoxy, i.e., alkoxy having 1 to 4 carbon atoms, e.g., methoxy, ethoxy, isopropoxy and the like;
Ar is

or

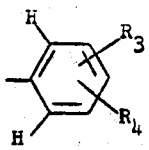

where
$R_3$ and $R_4$ each independently represent hydrogen, fluorine, chlorine, lower alkyl, i.e., alkyl having 1 to 4 carbon atoms, e.g., methyl ethyl, isopropyl and the like or lower alkoxy, as defined above, provided that at least one of $R_3$ and $R_4$ is other than hydrogen and that when $R_3$ and $R_4$ are both tertiary butyl, they are on other than adjacent carbon atoms,
or a pharmaceutically acceptable acid addition salt thereof.

The compounds of formula (I) in which $R_3$ and $R_4$ are each independently hydrogen, fluorine, or chlorine, wherein at least one of $R_3$ and $R_4$ is fluorine or chlorine are particularly preferred. The compounds in which $R_3$ and/or $R_4$ are chlorine are especially preferred.

The compounds of formula (I) may be prepared by the following reaction scheme:

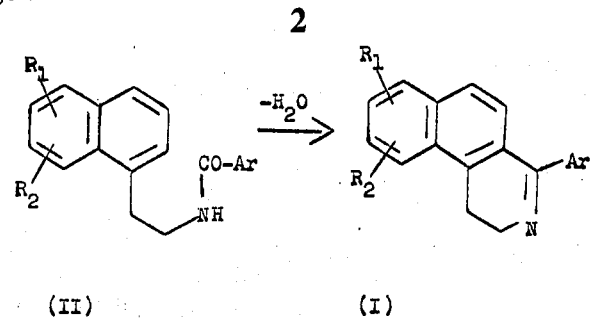

where $R_1$, $R_2$, Ar and the proviso are as set out above.

The compounds of formula (I) are prepared by treating a compound of formula (II) with an acidic cyclizing agent. The cyclizing agent can be any of the conventional acidic cyclizing agents such as thionyl chloride, phosphorus oxychloride, phosphorus pentachloride or preferably polyphosphoric acid. The polyphosphoric acid can be any of the known polyphosphoric acids or modified polyphosphoric acids. Although a solvent is not essential, it is preferred that the reaction be run in excess cyclizing agent. If desired, an inert solvent such as the hydrocarbons, e.g. hexane, heptane, etc, aromatic hydrocarbons, e.g., benzene, toluene and the like; a halogenated aliphatic hydrocarbon such as methylene dichloride or ethers, e.g., dioxane, tetrahydrofuran and the like can be used as the solvent or as a cosolvent. The temperature the reaction is run at is not critical, but it is preferred that the reaction be carried out between 80° and 200° C, especially between 100° and 150° C. For optimum results, the reaction should be run for 30 minutes to about 24 hours, preferably 1 to 6 hours. The product (I) is recovered by conventional techniques, e.g., extraction and evaporation.

Many of the compounds of formula (II) are known and are prepared by procedures disclosed in the literature. The compounds of formula (II) not specifically disclosed in the literature may be prepared by analgous methods using known starting materials.

The compounds of formula (I) are useful because they possess pharmacological activity in animals. In particular, the compounds are useful as anti-fertility agents as indicated by their activity in female Wistar rats which are injected daily with 2 mg. of the compound for 14 successive days starting on the day of vaginal cornification. At the time of the 4th injection, males of known fertility are cohabitated with the females (one female with one male) until the end of the treatment period. The males remain with the females until the third day following the last injection at which time the females are sacrificed and examined for the presence or absence of implantation sites.

The use of the compounds as anti-fertility agents is further indicated by their luteolytic properties which results in the compounds being abortifacient agents. The luteolytic activity is determined using pseudopregnant rabbits treated with corn oil or compound of formula (I) (1–100 mg. per day) suspended in corn oil on days 3 through 8 of pseudopregnancy. Blood samples are obtained daily throughout the length of pseudopregnancy. Plasma samples are analyzed for progestin content according to the method of Johansson et al. (Endocrinology 82, 143, 1968) or for progesterone content according to the method of Thorneycraft and Stone (Contraception, 5, 129–146 [1972]). The compound is judged active if plasma progestin levels are similar to pretreatment values on day 12 of pseudopregnancy.

Abortifacient activity is also determined in female proestrous rats (Royal Hart, Wistar strain) selected from a colony and caged with fertile males. On the following day, pregnancy is confirmed by the presence of spermatozoa on the vaginal smear. On the seventh day following mating, the females are treated with 1 to 30 milligrams of the compound to be tested. The animals are injected daily for a total of 7 days; and on the eighth day following the first injection, the animals are sacrificed and the uterus checked for the presence of absence of implantation sites.

The compounds of formula (I), when used as anti-fertility agents, exhibit none of the estrogenic effects and side effects exhibited by the steroidal type compounds used for these purposes.

When the compounds are employed for the above utility, they may be combined with one or more pharmaceutically acceptable carriers or adjuvants, and may be administered orally in such forms as tablets, capsules, elixirs, suspensions and the like, e.g., bucally or sub-lingually as a tablet, parenterally in the form of an injectable solution or suspension or in special forms such as suppositories, e.g., vaginal inserts, pessaries, and the like. Depending upon the compound employed and the mode of administration the exact dosage utilized may vary.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly, are included within the scope of the invention. Representative of the acid addition salts are the mineral acid salts, such as the hydrochloride, hydrobromide, sulfate, phosphate and the like and the organic acid salts, such as the succinate, benzoate, acetate, p-toluenesulfonate, benzenesulfonate, and the like.

In general, satisfactory results are obtained when the compounds of formula (I) are administered as anti-fertility agents at a daily dosage of about 1.0 milligrams to about 200 milligrams orally, subcutaneously or intramuscularly per kilogram of animal body weight. This daily dosage is preferably administered 1 to 4 times a day or in sustained release form. For most large mammals, such as primates, the total daily dosage is from about 1 milligram to about 600 milligrams. Dosage forms suitable for internal use comprise from about 0.25 milligrams to about 300 milligrams of the active compound in intimate admixture with a solid or liquid pharmaceutically acceptable carrier or diluent.

A representative formulation suitable for intramuscular administration once a day in fertility control is an injectable suspension prepared by standard techniques which contain the following:

| Ingredients | Weight (mg) |
| --- | --- |
| 4-(p-chlorophenyl)-1,2-dihydrobenz[f]isoquinoline | 200 |
| sodium carboxy methyl cellulose U.S.P. | 1.25 |
| methyl cellulose | 0.4 |
| polyvinylpyrrolidone | 5 |
| lecithin | 3 |
| benzyl alcohol | 0.01 |
| buffer agent to adjust pH for desired stability | q.s. |
| water | for injection q.s. to 2 ml. |

EXAMPLE 1

4-(p-chlorophenyl)-1,2-dihydrobenz[f]isoquinoline

Step A: N-(p-chlorobenzoyl)-α-naphthylethylamine

To a stirred solution of 23.6 grams (0.138 mole) of α-naphthylethylamine and 20.2 grams (0.20 mole) triethylamine in 150 ml of dry benzene, there is added dropwise a solution of 24.8 grams (0.142 mole) of p-chlorobenzoyl chloride in 150 ml of benzene. After stirring overnight at room temperature the salts are filtered off and the filtrate is concentrated in vacuo. The resultant residue is crystallized from methylene chloride/hexane to give N-(p-chlorobenzoyl)-α-naphthylethylamine, m.p. 117°–118° C.

Following the above procedure but using an equivalent amount of:
 a. p-toluoyl chloride;
 b. p-methoxybenzoyl chloride;
 c. isonicotinoyl chloride;
 d. 2-thenoyl chloride;
 e. p-fluorobenzoyl chloride,
 f. 3,4-dichlorobenzoyl chloride or
 g. m-chlorobenzoyl chloride
in place of the above p-chlorobenzoyl chloride, there is obtained
 a. N-(p-toluoyl)-α-naphthylethylamine;
 b. N-(p-methoxybenzoyl)-α-naphthylethylamine;
 c. N-(2-thenoyl)-α-naphthylethylamine;
 d. N-(2-thenoyl)-α-naphthylethylamine;
 e. N-(p-fluorobenzoyl)-α-naphthylethylamine;
 f. N-(3,4-dichlorobenzoyl)-α-naphthylethylamine, or
 g. N-(m-chlorobenzoyl)-α-naphthylethylamine, respectively When the above process is carried out using an equivalent amount of 6-methoxy-α-naphthylethylamine in place of the above α-naphthylethylamine, there is obtained N-(p-chlorobenzoyl)-6-methoxy-α-naphthylethylamine.

Step B: 4-(p-chlorophenyl)-1,2-dihydrobenz[f]isoquinoline

A mixture of 4.0 grams of N-(p-chlorobenzoyl)-α-naphthylethylamine and 80 grams of polyphosphoric acid is heated at 145° for about 2 hours. The mixture is cooled to about 55°, treated slowly with 500 ml of water and then extracted twice with 100 ml of ether. The acid layer is cooled in an icebath and treated with 50% aqueous sodium hydroxide until basic to litmus.

The basic phase is then extracted twice with 100 ml of methylene chloride. The methylene chloride extracts are combined, washed four times with 100 ml of water, dried with magnesium sulfate and filtered through celite. The filtrate is concentrated in vacuo and the residue is crystallized from methylene chloride/hexane to give 4-(p-chlorophenyl)-1,2-dihydrobenz[f]isoquinoline m.p. 138°–140° C.

Following the above procedure, but using an equivalent amount of:
a. N-(p-toloyl)-α-naphthylethylamine;
b. N-(p-methoxybenzoyl)-α-naphthylethylamine;
c. N-isonicotinoyl-α-naphthylethylamine;
d. N-(2-thenoyl)-α-naphthylethylamine;
e. N-(p-chlorobenzoyl)-6-methoxy-α-naphthylethylamine;
f. N-(p-fluorobenzoyl)-α-naphthylethylamine;
g. N-(3,4-dichlorobenzoyl)-α-naphthylethylamine, or
h. N-(m-chlorobenzoyl)-α-naphthylethylamine, respectively there is obtained
a. 4-(p-tolyl)-1,2-dihydrobenz[f]isoquinoline;
b. 4-(p-methoxybenzyl)-1,2-dihydrobenz[f]isoquinoline;
c. 4-(4-pyridyl)-1,2-dihydrobenz[f]isoquinoline;
d. 4-(2-thienyl)-1,2-dihydrobenz[f]isoquinoline;
e. 4-(p-chlorophenyl)-8-methoxy-1,2-dihydrobenz[f]isoquinoline,
f. 4-(p-fluorophenyl)-1,2-dihydrobenz[f]isoquinoline, (m.p. 121°–123° C)
g. 4-(3,4-dichlorophenyl)-1,2-dihydrobenz[f]isoquinoline, (m.p. 117°–118° C), or
h. 4-(m-chlorophenyl)-1,2-dihydrobenz[f]isoquinoline, (m.p. 93°–95° C), respectively.

The 4-(p-chlorophenyl)-1,2-dihydrobenz[f]isoquinoline of this example is an effective anti-fertility agent when administered to a female mammal at a dosage of 25 milligrams 2 to 4 times a day.

What is claimed is:
1. A compound of the formula:

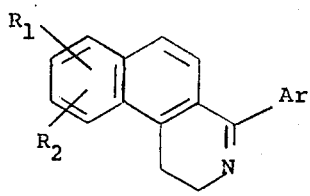

where
$R_1$ and $R_2$ each independently represent hydrogen or lower alkoxy having 1 to 4 carbon atoms,
Ar is

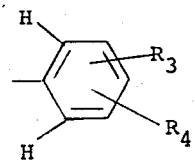

and
$R_3$ and $R_4$ are each independently hydrogen, fluorine or chlorine
provided that at least one of $R_3$ and $R_4$ is fluorine or chlorine or a pharmaceutically acceptable acid addition salt thereof.

2. A compound of claim 1 in which $R_3$ and $R_4$ are each independently hydrogen or chlorine wherein at least one of $R_3$ and $R_4$ is chlorine.

3. The compound of claim 1, which is 4-(p-chlorophenyl)-1,2-dihydrobenz[f]isoquinoline.

4. The compound of claim 1, which is 4-(p-fluorophenyl)-1,2-dihydrobenz[f]isoquinoline.

5. The compound of claim 1, which is 4-(3,4-dichlorophenyl)-1,2-dihydrobenz[f]isoquinoline.

6. The compound of claim 1, which is 4-(m-chlorophenyl)-1,2-dihydrobenz[f]isoquinoline.

* * * * *